United States Patent [19]
Blackwell et al.

[11] Patent Number: 5,347,431
[45] Date of Patent: Sep. 13, 1994

[54] LIGHTING SYSTEM AND CAMERA FOR OPERATING ROOM

[76] Inventors: Ray A. Blackwell, 350 E. 17th St., New York, N.Y. 10003; Peter J. Wilk, 185 West End Ave., New York, N.Y. 10023

[21] Appl. No.: 810,831

[22] Filed: Dec. 20, 1991

[51] Int. Cl.⁵ ............................................. F21V 21/14
[52] U.S. Cl. ...................................... 362/11; 362/231; 362/233; 362/286; 362/804; 354/81
[58] Field of Search ............... 362/11, 18, 231, 233, 362/286, 428, 804; 128/23; 354/74, 75, 76, 81

[56] References Cited
U.S. PATENT DOCUMENTS

| | | | |
|---|---|---|---|
| 3,399,614 | 9/1968 | Fischer | 354/81 |
| 3,702,928 | 11/1972 | Alger | 362/804 |
| 3,891,842 | 6/1975 | Strusinski | 362/18 |
| 4,196,460 | 4/1980 | Schreckendgust | 362/231 |
| 4,384,315 | 5/1983 | Hayakawa | 362/804 |
| 4,519,021 | 5/1985 | Oram | 362/286 |
| 4,578,575 | 3/1986 | Roos | 362/286 |
| 4,616,257 | 10/1986 | Kloots et al. | 362/32 |
| 5,038,261 | 8/1991 | Kloos | 362/286 |
| 5,073,824 | 12/1991 | Vertin | 358/210 |
| 5,093,769 | 3/1992 | Luntsford | 362/804 |

Primary Examiner—Ira S. Lazarus
Assistant Examiner—L. Heyman
Attorney, Agent, or Firm—R. Neil Sudol; Henry D. Coleman

[57] ABSTRACT

A lighting system for a surgical operating room comprises a light source for emitting electromagnetic radiation, a support for holding the light source above an operating table in the operating room, the light source being movably mounted to the support, and a drive operatively coupled to the light source for automatically moving the light source relative to the support. An activator or control disposed in proximity to the operating table is operatively connected to the drive for controllably energizing the drive in response to manipulations by a surgeon working at the operating table.

12 Claims, 1 Drawing Sheet

LIGHTING SYSTEM AND CAMERA FOR OPERATING ROOM

BACKGROUND OF THE INVENTION

This invention relates to a lighting system. More particularly, this invention relates to a lighting system for a surgical operating room. This invention also relates to a camera system specifically for an operating room.

Operating rooms in hospitals are provided with ceiling lights which are manually directed and redirected, generally by operating room assistants in response to commands provided by an operating surgeon. The lighting is therefore inexact and inefficient. Time must be expended in ensuring that the lights are directed to the appropriate locations of a patient's anatomy.

It is also desirable during surgery to obtain a photographic record of different surgical sites in a patient at different stages of an operation. As with the lighting, cameras are usually activated by assistants who must be verbally instructed as to the subjects of which the surgeons wish pictures to be taken. Such relatively primitive methods require excessive amounts of time to ensure that the proper photographs are taken.

OBJECTS OF THE INVENTION

An object of the present invention is to provide an improved lighting system for an operating room and an associated method for illuminating a patient during surgery.

Another object of the present invention is to provide a method and system for lighting an operating room which is quick and accurate in its implementation.

Another, more particular, object of the present invention is to provide such a method and system which are versatile.

Yet another object of the present invention is to provide a method and system for facilitating the taking of photographs of a patient during surgery.

SUMMARY OF THE INVENTION

A lighting system for a surgical operating room comprises, in accordance with the present invention, a light source for emitting electromagnetic radiation, a support for holding the light source above an operating table in the operating room, the light source being movably mounted to the support, and a drive operatively coupled to the light source for automatically moving the light source relative to the support. An activator or control disposed in proximity to the operating table is operatively connected to the drive for controllably energizing the drive in response to manipulations by a surgeon working at the operating table.

Preferably, the support includes an elongate track mounted to a ceiling of the operating room. The track may take virtually any shape or configuration. For example, the track may be partially or completely circular or linear. In addition, the track may have a portion extending downwardly away from the ceiling.

Pursuant to another feature of the present invention, at least an output portion of the light source is pivotably and translatably mounted to the track. The drive includes a translatory drive component for automatically shifting the output portion of the light source along the track and further includes a rotary drive component for automatically pivoting the output portion of the light source relative to the track.

In addition, the light source may be a cold light source, that is, it may include a remote light generator and an optical fiber connecting the light generator to the output portion of the source.

Preferably, the activator includes at least one manual actuator located in proximity to the operating table. The actuator may thus include levers or pushbuttons or a joystick.

A disposable cover is advantageously connectable to the activator for protecting the actuator from contamination. The cover is preferably made at least in part of a transparent flexible film material.

Pursuant to another feature of the present invention, a plurality of light sources are mounted to the support track or tracks, each light source being shiftable along the respective track and pivotable with respect thereto. The light sources on the track or tracks may have different ranges of light frequencies. For example, one source may be an ultraviolet light for energizing phosphorescent or fluorescent dyes in a patient's blood stream.

According to another feature of the present invention, a light source is mounted to a camera for enabling an operator to remotely aim the camera by manipulating the activator at the operating table. In this case, the camera is movably mounted to the support and the drive is operatively connected to the camera.

The camera is preferably supplemental to the principal light sources. The support track or tracks thus carry both light sources and a camera.

A camera assembly for a surgical operating room accordingly comprises, in accordance with the present invention, a camera, a support for holding the camera above an operating table in the operating room, the camera being movably mounted to the support, and a drive operatively coupled to the camera for automatically moving same relative to the support. An activator or control disposed on or about the operating table is operatively connected to the drive for controllably energizing the drive and for actuating the camera in response to manipulations by a surgeon working at the operating table.

As discussed hereinabove, the support preferably includes an elongate curved or straight track mounted to a ceiling of the operating room, while the camera is pivotably and translatably mounted to the track.

As further discussed hereinabove, the camera preferably includes a light source for emitting a beam of light to facilitate aiming of the camera.

A method for lighting a surgical operating room comprising the steps of (a) operating a light source, located generally above an operating table in the operating room, to emit a beam of electromagnetic radiation, (b) manipulating a control element at an operating table in the operating room, and (c) in response to the step of manipulating, automatically moving at least an output element of the light source to change the direction of the beam and concomitantly objects illuminated by the beam.

Pursuant to another feature of the present invention, the step of moving includes the steps of translating the output element along a predefined track and pivoting the output element relative to the track.

The method may further comprise the step of manipulating an additional control element to automatically activate a camera to take a photograph of objects illuminated by the beam.

The present invention provides a surgeon controlled lighting system for an operating room and an associated method for illuminating a patient during surgery. Because the system may be operated directly by the surgeon, the effectiveness of the lighting is enhanced. The lighting is implemented immediately and automatically in response to the surgeon's manipulation of one or more levers or other actuators (e.g., foot pedals). There is no necessity for voice communication. This method thereby eliminates the delays inherent in instructing other people and increases the accuracy of the lighting.

A system in accordance with the present invention is versatile in that it enables the automatic adjustment and positioning of lights of different frequency ranges. The lights may be provided with filters which are automatically activated.

A method and system in accordance with the present invention also facilitates the taking of photographs of a patient during surgery. Through the use of a spotting beam, the operating surgeon is able to obtain immediate feedback as to the subject of a photograph, prior to the taking of the photograph. The surgeon operates and aims the camera, as well as the light sources, via remote control.

An advantage of a lighting or camera system in accordance with the present invention is that the assistants in the operating room need not crowd the operating surgeon(s) at the operating table. In conventional operating room procedures, assistants who are responsible for the adjustment of the lights and the operation of the cameras must look over the shoulders of the surgeon(s) to determine whether the lights and camera are accurately aimed.

Thus, the system and method of the present invention increases the space around an operating table, making it available for other activities and procedures.

DETAILED DESCRIPTION

Figure 1:
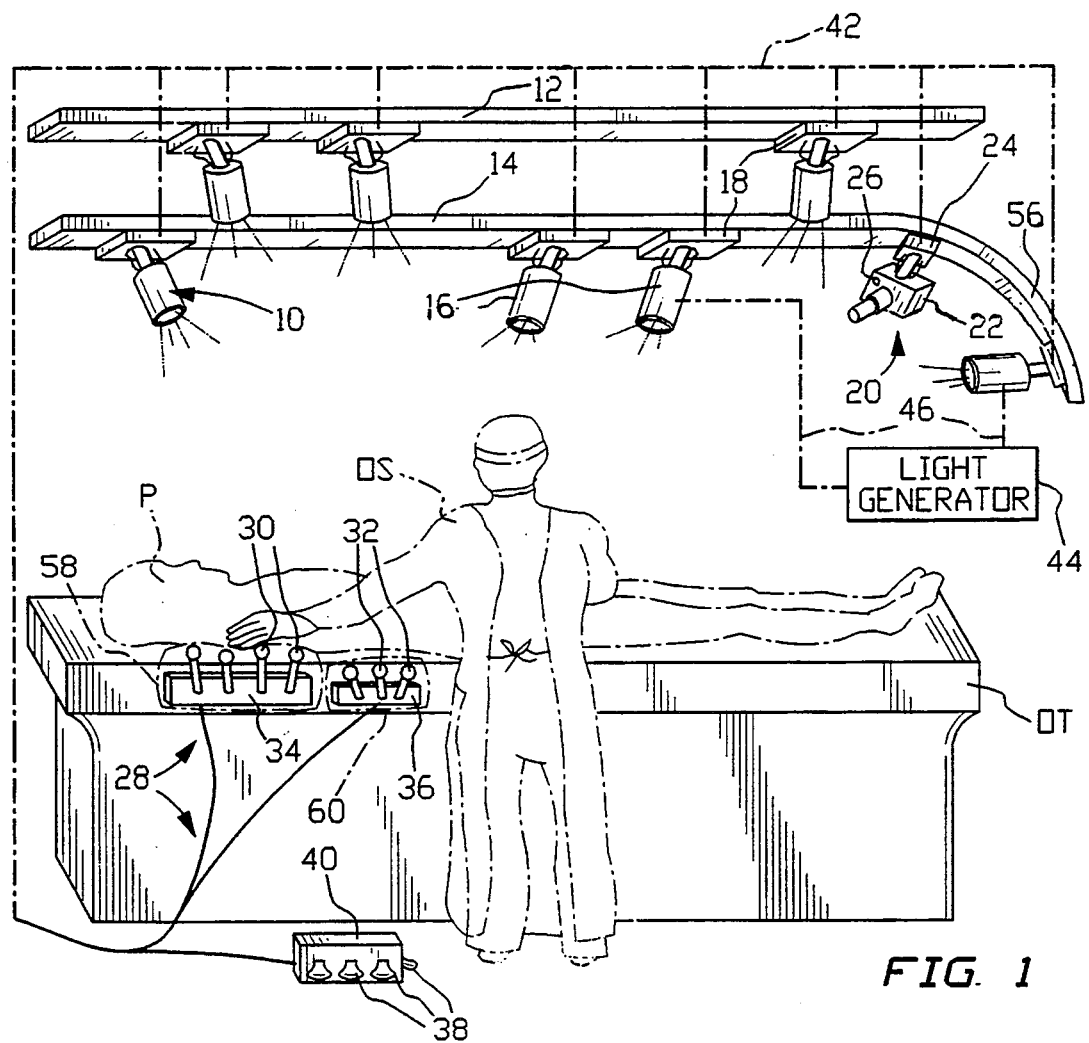
FIG. 1 is a schematic perspective view of a lighting and photography system for an operating room, in accordance with the present invention.

As illustrated in FIG. 1, a lighting and photography system for a surgical operating room comprises a plurality of light sources 10 each movably attached to one of a plurality of support tracks or rails 12 and 14 in turn fixed to a ceiling of the operating room over an operating table OT. Each light source 10 includes a casing 16 pivotably attached to a respective carrier or trolley 18 which is translatably mounted to track 12 or 14.

The lighting and photography system further comprises a camera 20 movably mounted to rail 14. Camera 20 includes a casing 22 pivotally attached to a respective carrier or trolley 24 which is translatably mounted to track 14. Camera 20 additionally includes a laser source 26 which generates a spotting beam for enabling or facilitating an aiming of the camera.

The positions of trolleys 18 and 24 along tracks 12 and 14, as well as the rotational orientations of casings 16 and 22 relative to tracks 12 and 14, are adjustable by an operating surgeon OS via a control unit or assembly 28. Control unit or assembly 28 comprises a plurality of manually actuatable activation levers 30 and 32 attached to operating table OT via a pair of housings 34 and 36. Control unit or assembly 28 additionally or alternatively comprises a plurality of foot pedals 38 disposable adjacent operating table OT in a housing 40 operatively connected via a multiple line 42, as are housings 34 and 36, to trolleys 18 and 24 and casings 16 and 22.

Casings 16 may function as output elements of cold light assemblies. In that event, a remote light generator 44 is connected to the casings via optical fibers 46.

Figure 2:
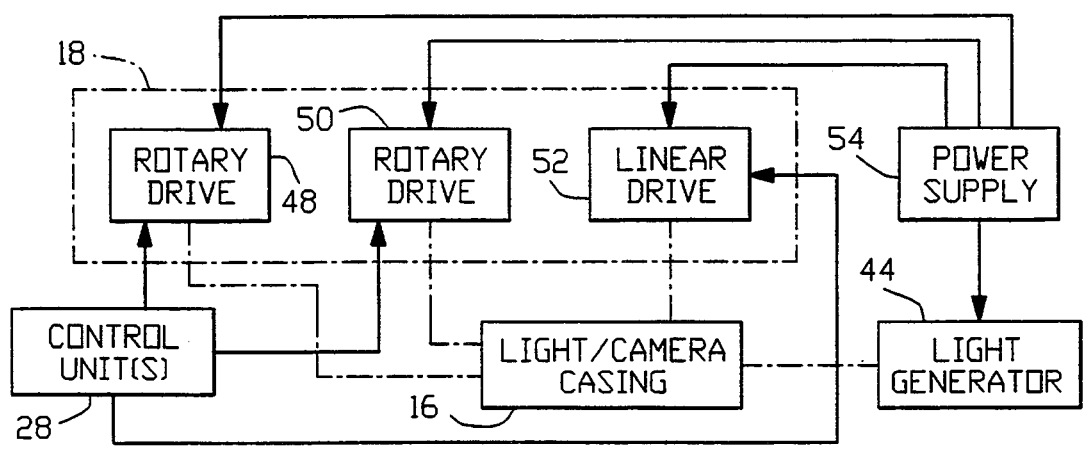
FIG. 2 is a block diagram of functional components of the system of FIG. 1.

As shown in FIG. 2, each trolley 18 and 24 carries a pair of rotary drives 48 and 50 for pivoting the respective light or camera casing 16 or 22 about a pair of rotational axes (not indicated) and a translatory or linear drive 52 for shifting the trolley 18 or 24 and the associated light or camera casing 16 or 22 longitudinally along the respective track 12 or 14. Rotary drives 48 and 50 could be alternatively housed in the casings 16 and 22.

Drives 48, 50 and 52 are operatively connected to a power supply 54. In response to control or energizing signals from control unit 28, drives 48, 50 and 52 are activated to change the positions and orientations of light and camera casings 16 and 22 relative to tracks 12 and 14. This positional control is implemented quickly and accurately.

As illustrated in FIG. 1, track 14 has a downwardly arcing terminal portion 56 which enables the positioning of a light source to effectively illuminate vertically extending surfaces of a patient P, such as around the patient's rectal area or flanks. In addition, camera 20 may be more effectively positioned to photograph such surfaces or areas.

As further illustrated in FIG. 1, disposable covers 58 and 60 are removably connected to actuator housings 34 and 36 for protecting levers 30 and 32 from contamination. Preferably, covers 58 and 60 are made at least in part of a transparent flexible film material such as polyethylene. Covers 58 and 60 and actuator housings 34 and 36 may be provided with cooperating connectors (not shown) for facilitating the attachment and removal of the covers from the housings. Such connectors may take any conventional form, e.g., snap-lock, zip-lock, loop and hook (VELCRO). Alternatively, covers 58 and 60 may be provided with adhesive strips for releaseably attaching the covers to the respective housings 34 and 36.

Although the invention has been described in terms of particular embodiments and applications, one of ordinary skill in the art, in light of this teaching, can generate additional embodiments and modifications without departing from the spirit of or exceeding the scope of the claimed invention. For example, the number, shapes and locations of the lighting support tracks may be varied. The lights may have filters which are actuated via control unit 28. The light sources 10 may have different ranges of light frequencies. For example, one source 10' may be an ultraviolet light for energizing phosphorescent or fluorescent dyes in a patient's blood stream. In addition, camera 20 may take the form of a video camera, particularly a video camera feeding digitized color and light intensity signals to a color printer, or any other equivalent implementation for producing fixed images of a surgical site. Camera 20 in miniature form may alternatively be mounted to the surgeon's head.

Accordingly, it is to be understood that the drawings and descriptions herein are proferred by way of example to facilitate comprehension of the invention and should not be construed to limit the scope thereof.

What is claimed is:

1. A surgical lighting system, comprising:

light source means for emitting electromagnetic radiation, said light source means including an output portion and a remote light generator and additionally including a plurality of optical fibers connecting said light generator to said output portion;

support means for holding said output portion above an operating table in an operating room, said output portion being movably mounted to said support means;

drive means operatively coupled to said light source means for automatically moving said output portion relative to said support means;

activation means operatively connected to said drive means for controllably energizing said drive means in response to manipulations by a surgeon working at the operating table; and disposition means operatively linked to said activation means for enabling disposition thereof in proximity to the operating table.

2. The system defined in claim 1 wherein at least an output portion of said light source means is pivotably and translatably mounted to said track, said drive means including translation means for shifting said output portion of said light source means along said track, said drive means further including rotation means for pivoting said output portion of said light source means relative to said track.

3. The system defined in claim 1 wherein said track includes a section extending downwardly from said ceiling.

4. The system defined in claim 1 wherein said activation means includes at least one manual actuator located in proximity to the operating table.

5. The system defined in claim 4, further comprising a disposable cover connectable to said activation means for protecting said actuator from contamination.

6. The system defined in claim 4 wherein said disposition means includes mounting means for mounting said actuator to said operating table.

7. The system defined in claim 1 wherein said activation means includes at least one foot pedal.

8. The system defined in claim 1, further comprising camera means for taking a photograph, said camera means being movably mounted to said support means, said drive means being operatively connected to said camera means for moving same relative to said support means, said activation means being operable to control motion and operation of said camera means.

9. The system defined in claim 1 wherein said light source means includes a first generator of light having a first range of frequencies and a first output portion and a second generator of light having a second range of frequencies and a second output portion, said second range of frequencies being different from said first range, said first output portion and said second output portion being independently movable by said drive means in response to manipulations of said activation means.

10. A surgical lighting system, comprising:

light source means for emitting electromagnetic radiation;

support means for holding said light source means above an operating table in an operating room, said light source means being movably mounted to said support means, said support means including a track mounted to a ceiling of the operating room, said track having a section extending downwardly from said ceiling;

drive means operatively coupled to said light source means for automatically moving same relative to said support means;

activation means operatively connected to said drive means for controllably energizing said drive means in response to manipulations by a surgeon working at the operating table; and disposition means operatively linked to said activation means for enabling disposition thereof in proximity to the operating table.

11. A surgical lighting system, comprising:

light source means for emitting electromagnetic radiation;

support means for holding said light source means above an operating table in an operating room, said light source means being movably mounted to said support means;

first drive means operatively coupled to said light source means for automatically moving same relative to said support means;

activation means operatively connected to said drive means for controllably energizing said drive means in response to manipulations by a surgeon working at the operating table;

disposition means operatively linked to said activation means for enabling disposition thereof in proximity to the operating table;

camera means for taking a photograph, said camera means being mounted to said support means for motion relative to said support meanas independently of said light source means; and second drive means different from said first drive means and operatively connected to said camera means for moving same relative to said support means, said activation means being connected to said second drive means for controlling motion and operation of said camera means.

12. A lighting system for a surgical operating room, comprising:

light source means for emitting electromagnetic radiation;

support means for holding said light source means above an operating table in the operating room, said light source means being movably mounted to said support means;

drive means operatively coupled to said light source means for automatically moving same relative to said support means;

activation means operatively connected to said drive means for controllably energizing said drive means in response to manipulations by a surgeon working at the operating table, said activation means including at least one manual actuator located in proximity to the operating table; and disposition means operatively linked to said activation means for enabling disposition thereof in proximity to the operating table, said disposition means including mounting means for mounting said actuator to said operating table.

* * * * *

UNITED STATES PATENT AND TRADEMARK OFFICE
CERTIFICATE OF CORRECTION

PATENT NO. : 5,347,431
DATED : September 13, 1994
INVENTOR(S) : Ray A. Blackwell and Peter J. Wilk It is certified that error appears in the above-indentified patent and that said Letters Patent is hereby corrected as shown below:

```
    Column 6, line 37, claim 11, change "meanas" to
--means--.
```

Signed and Sealed this

Fourth Day of April, 1995

Attest:

BRUCE LEHMAN

*Attesting Officer*   *Commissioner of Patents and Trademarks*